US010619298B2

(12) United States Patent
Tausche et al.

(10) Patent No.: US 10,619,298 B2
(45) Date of Patent: Apr. 14, 2020

(54) ENZYMATIC TREATMENT OF VIRGIN FIBER AND RECYCLED PAPER TO REDUCE RESIDUAL MINERAL OIL LEVELS FOR PAPER PRODUCTION

(71) Applicant: Enzymatic Deinking Technologies, L.L.C., Norcross, GA (US)

(72) Inventors: James G. Tausche, Atlanta, GA (US); Jianhua Ma, Alpharetta, GA (US); Chengliang Jiang, Duluth, GA (US)

(73) Assignee: Enzymatic Deinking Technologies, L.L.C., Norcross, GA (US)

( * ) Notice: Subject to any disclaimer, the term of this patent is extended or adjusted under 35 U.S.C. 154(b) by 820 days.

(21) Appl. No.: 14/547,006

(22) Filed: Nov. 18, 2014

(65) Prior Publication Data

US 2015/0136343 A1   May 21, 2015

Related U.S. Application Data

(60) Provisional application No. 61/905,843, filed on Nov. 18, 2013.

(51) Int. Cl.
| | |
|---|---|
| *D21C 5/00* | (2006.01) |
| *D21C 9/08* | (2006.01) |
| *D21H 17/00* | (2006.01) |
| *C12N 9/00* | (2006.01) |
| *D21H 27/00* | (2006.01) |
| *D21H 11/14* | (2006.01) |
| *D21C 5/02* | (2006.01) |
| *D21H 27/10* | (2006.01) |

(52) U.S. Cl.
CPC .............. *D21C 5/005* (2013.01); *C12N 9/00* (2013.01); *D21C 5/02* (2013.01); *D21C 9/08* (2013.01); *D21C 9/086* (2013.01); *D21H 11/14* (2013.01); *D21H 17/005* (2013.01); *D21H 27/002* (2013.01); *D21H 27/10* (2013.01); *Y02W 30/648* (2015.05)

(58) Field of Classification Search
CPC ............ D21C 9/08; D21C 9/086; D21B 1/32
See application file for complete search history.

(56) References Cited

U.S. PATENT DOCUMENTS

| 5,507,914 | A * | 4/1996 | Sarkar ................. D21C 5/005 162/100 |
| 6,967,246 | B2 | 11/2005 | Swanson |
| 2006/0048908 | A1 * | 3/2006 | Wang ................... D21C 9/08 162/199 |
| 2006/0102299 | A1 | 5/2006 | Elgarhy |
| 2007/0111920 | A1 | 5/2007 | Baur et al. |
| 2013/0017584 | A1 * | 1/2013 | Hofrichter ................ C12P 7/04 435/146 |
| 2013/0146239 | A1 | 6/2013 | Tausche |

FOREIGN PATENT DOCUMENTS

| WO | 2006029404 | 3/2006 |
| WO | 2010010343 | 1/2010 |
| WO | 2010093233 | 8/2010 |
| WO | 2011100530 | 8/2011 |
| WO | 2013045782 | 4/2013 |
| WO | 2013090272 | 6/2013 |
| WO | 2014058581 | 4/2014 |

OTHER PUBLICATIONS

Ewald et al., Mineral Oil Removal in Recovered Paper Processing, Sep. 18, 2013, 10th Research Forum on Recycling.*
Smook, Handbook for Pulp and Paper Technologists, 1992, Angus Wilde Publications, 2nd edition, chapter 17.*
Glieder et al., Laboratory evolution of a soluble, self-sufficient, highly active alkane hydroxylase, 2002, Nature biotechnology, vol. 20, p. 1135-1139.*
Zhang, et al., "Cellulase deinkng of fresh and aged recycled newsprint/magazines", Enzyme Microbial Tech., 43(2):103-8 (20008).
International Search Report and Written Opinion for PCT/US2014/066216 dated Mar. 26, 2015.
Biedermann and Grob, "Is recycled newspaper suitable for food contact materials?" , Eur. Food Res. Technol., 230:785-96 (2010).
Biedermann, et al., "Mineral oil contents in paper and board recycled to paperboard for food packaging" , Packag. Technol. Sci., 24(2)61-73 (2011).
Biedermann and Grob, "On-line coupled high performance liquid chromatography-gas chromatography for the analysis of contamination by, mineral oil. Part 1: Method of analysis", J Chromatography A, http://dx.doi.org/1.1016/j.chroma.2012.05.095(2012).

(Continued)

*Primary Examiner* — Anthony Calandra
(74) *Attorney, Agent, or Firm* — PABST Patent Group LLP

(57) ABSTRACT

Compositions comprising enzyme compositions are provided. Also provided are methods of treating virgin fiber and recycled wastepaper containing mineral oils using the compositions comprising enzyme compositions. The mineral oils generally originate from wastepapers with mineral oil based inks and certain other hydrocarbon-based chemistries used during the manufacturing, paperboard converting, and packaging process. The enzymes break down or modify mineral oils present in the fiber and paper, mobilize and liberate them from the fibers, and increase removal of mineral oils during paper recycling, pulping and papermaking processes. The method results in the break down or modification of mineral oil components in wastepaper, recycled pulp, and paper products by the enzyme compositions so that the mineral oils can be more efficiently detached and removed. The resulting pulp and paper has much reduced mineral oil concentration or less problematic forms of mineral oils and is beneficial for making food packaging paper products.

44 Claims, No Drawings

(56) References Cited

OTHER PUBLICATIONS

Biedermann-Brem and Grob, "Removal of mineral oil migrated from paperboard packing during cooking of foods in boiling water", Eur. Food Res. Technol., 232:1035-41 (2011).

Droz and Grob, "Determination of food contamination by mineral oil material from printed cardboard using on-line coupled LC-GC-FID", Eur. Food Res. Technol., 205:239-41 (1997).

EFSA, Scientific Opinion on Mineral Oil Hydrocarbons in Food, EFSA Journal 2012; 10 (6): 2704).

Grob, et al., "Food contamination by hydrocarbons from lubricating oils and release agents: Determination by coupled LC GC", Food Additives and Contaminants, 8(4):437-46 (1991).

Jamnicki, "Determination of Mineral Oil Content in Recycled Papers", EFPRO "CEPI Innovation in Paper" Early Stage Researcher (ESR) WorkshopEurpean, PaperWeek, Nov. 13-15 Brussels (2012a).

Jamnicki, "Determination of mineral oil content in recycled papers: Report of the short term scientific mission", Eu Fibre Paper Res. Org., Heidenau-Dresden, Germany, Aug. 25, 2012 thru Sep. 8m, 2012.

Lorenzini, et al., "Saturated and aromatic mineral oil hydrocarbons from paperboard food packaging; estimation of long-term migration from contents in the paperboard and data on boxes from the market", Food Additives and Contaminants, Part A, 27(12):1765-74 (2010).

Vollmer and Biedermann, "Migration of mineral oil from printed paperboard into dry foods: survey of the German market", Euri Food Res. Technol., 232:175-182 (2011).

\* cited by examiner

ENZYMATIC TREATMENT OF VIRGIN FIBER AND RECYCLED PAPER TO REDUCE RESIDUAL MINERAL OIL LEVELS FOR PAPER PRODUCTION

CROSS-REFERENCE TO RELATED APPLICATIONS

This application claims benefit of U.S. Provisional Application No. 61/905,843, filed Nov. 18, 2013. Application No. 61/905,843, filed Nov. 18, 2013, is hereby incorporated herein by reference in its entirety.

FIELD OF THE INVENTION

The present invention is generally in the field of pulping and papermaking, including waste paper and paperboard recycling; and more specifically in the field of treating wood and non-wood fibers and recycled waste paper containing mineral oil based printing inks with enzymes to break down and/or modify mineral oil components present in the wood and non-wood pulp and wastepaper for their enhanced removal during the paper recycling, pulping, and papermaking process.

BACKGROUND OF THE INVENTION

Mineral oils in food grade paper and paperboard products primarily originate from printing inks and grease and certain other hydrocarbon-based chemistries used during the manufacturing, paperboard converting, and packaging process. Old corrugated container (OCC) makes up a significant part of the recycled waste paper stream. Some of the recycling mills may also use mixed papers that may contains over 50-90% ONP/OMG (old newspaper and old magazine). OCC recycling mills are operated very differently than conventional mixed paper recycling mills. As a result, most printing inks are left in the recycled pulping and papermaking processes and end up in the recycled paper products. This is one of the main reasons why there is a high content of residual printing inks, wax, sizing and coating chemicals and other impurities on the recycled fibers in OCC recycling mills. These impurities may end up in many food grade papers and paperboard, such as the food packaging boxes for cereal, pizza, and frozen food.

Mineral oils (mineral oil hydrocarbons, MOH) are the by-products of petroleum distillation of hydrocarbons. The major components of the mineral oils are mineral oil saturated hydrocarbons (MOSH) and mineral oil aromatic hydrocarbons (MOAH). MOSH includes paraffins (linear or branched alkanes) and naphthenes (alkyl-substituted cycloalkanes), and MOAH (mainly alkyl-substituted polyaromatic hydrocarbons). In general, MOH are considered medically problematic, with some forms likely more problematic than others (EFSA, Scientific Opinion on Mineral Oil Hydrocarbons in Food, EFSA Journal 2012; 10 (6): 2704). For example, MOAH are considered more problematic than MOSH, MOH with rings are generally considered more problematic than MOH without rings, and more saturated MOH are considered more problematic than less saturated MOH.

Zurich's Official Food Control Authority has published two studies on the issue of the mineral oil migration (Biedermann et al. (2011), Mineral oil contents in paper and board recycled to paperboard for food packaging. Packag. Technol. Sci., 24: 61-73. doi: 10.1002/pts. 914; Biedermann, M. and Grob, K. (2010), Is recycled newspaper suitable for food contact materials? Eur. Food Res. Technol., 230: 785-796) which highlighted the inclusion of mineral oil in old newspapers in recycled paper and board as the main source of the potentially harmful oils. A survey of packaging of the German market identified mineral oil contamination in 119 samples of dry food packed in paperboard boxes (Vollmer et al., Eur Food Res Technol (2011) 232: 175-182). An analytical method for detecting the mineral oil content in paperboard packaging has been developed (Bundesinstitut für Risikobewertung (BfR), 2011). A substantial proportion of the offset printing inks applied to food packaging contained mineral oil, often including 15-20% MOAH (Vollmer et al., European Food Research and Technology, 232, 175-182 (2011)).

When foods in recycled board are densely packed into larger boxes or onto pallets, most of the hydrocarbons up to n-C20 may migrate into the packed food within a few weeks and those up to n-C28 at a slightly lower rate. The main sources of mineral oils in recycled paper are the inks used for printing newspapers: newspapers may contain roughly 3,000 mg/kg mineral oil hydrocarbons <n-C28. These mineral oils fall into classes for which JECFA established a tolerable daily intake of 0.01 mg/kg body weight. The oils found in recycled board contain 15-25% aromatic compounds, predominantly with 1-3 aromatic rings.

Since freshly packed foods are usually packed into larger transport boxes and stacked onto pallets, most of the mineral oil migrates inwards into the foods if not blocked by a barrier layer between the food and the print layer. Contamination of dry foods in paperboard boxes at concentrations sometimes exceeding 100 mg/kg was shown in studies by Grob et al. (Food Additives and Contaminants, 8, 437-446 (1991)) as well as Droz and Grob (Zeitschrift Fur Lebensmittel-Untersuchung Und-Forschung a-Food Research and Technology, 205, 239-241 (1997)). It was also shown that internal paper or polyethylene bags had little barrier effect.

Some of the foods packaged in paper and board packaging materials are consumed without further processing, such as cereals. Other foods, such as rice, are cooked before consumption. However, cooking in boiling water may remove only a part of the migrated MOH, perhaps because the MOH are located in the food matrix pores and water entering these pores is an almost perfect barrier to prevent MOH to be transferred into the boiling water (Biedermann-Brem and Grob, European Food Research and Technology 232, 1035-1041 (2011)).

Although it has been suggested that the problem of mineral oils in food packaging may be solved by using only virgin fiber for manufacture of food packaging, this is not cost-effective or practical. For example, the cost of virgin fiber is consistently many hundreds of dollars more expensive than recycled pulps. It has been estimated that exclusive use of virgin fiber for food packaging would require a doubling in worldwide tree production dedicated for paper packaging use. Increased use of virgin fiber would also reduce the demand for recycled paper with the result that more waste paper will end up in landfills or be incinerated. Finally, virgin fiber may not eliminate the problem of mineral oil in food as the process equipment and processing chemistries used for paper and paperboard production and conversion and in the packing process also contribute to the mineral oil levels in food packages. In one study, the initial concentration of MOSH<n-C24 in paperboard, the mean and maximum concentrations calculated for boxes largely consisting of recycled fibers (n=107), were 433 mg/kg paper and 1820 mg/kg paper respectively (Vollmer et al. (2011)). In boxes made of virgin fibers (n=13) the corresponding concentrations were 175 mg/kg paper and 402 mg/kg paper.

There is a need to produce pulp, board, and paper having reduced levels and less problematic forms of residual mineral oils.

It is therefore an object of this invention to provide enzyme compositions to treat the paper pulp and wastepaper during the recycling or papermaking process for reduced levels and/or less problematic forms of mineral oil hydrocarbons in processed pulp and paper products.

It is therefore an object of this invention to provide enzyme compositions to break down and/or modify the structure of mineral oil hydrocarbons for reduced levels and/or less problematic forms of mineral oil hydrocarbons in processed pulp and paper products.

It is therefore an object of this invention to provide enzyme compositions to mobilize and liberate mineral oil hydrocarbons in pulp for reduced levels and/or less problematic forms of mineral oil hydrocarbons in processed pulp and paper products.

It is therefore an object of this invention to provide a method using such enzyme compositions to break down and/or modify the structure of mineral oil hydrocarbons for reduced levels and/or less problematic forms of mineral oil hydrocarbons in processed pulp and paper products.

It is therefore an object of this invention to provide a method using such enzyme compositions to mobilize and liberate mineral oil hydrocarbons in pulp for reduced levels of mineral oil hydrocarbons in processed pulp and paper products.

It is therefore an object of this invention to provide a method using such enzyme compositions for reduced residual mineral oil levels in processed pulp and products.

It is therefore an object of this invention to provide a method using enzyme compositions and process steps to mobilize and liberate mineral oil hydrocarbons in pulp for reduced levels of mineral oil hydrocarbons in processed pulp and paper products.

It is also an object of this invention to provide processed pulp having lower levels of mineral oil hydrocarbons.

It is also an object of this invention to provide paper products made from pulp having lower levels of mineral oil hydrocarbons.

SUMMARY OF THE INVENTION

Methods of treating virgin fiber and waste paper with enzymes to break down, modify, liberate, and/or mobilize the mineral oil components present in the fiber, pulp, paper and pulping and papermaking process to increase removal of mineral oils during pulp processing and papermaking are provided. The methods provided decrease the level and/or change the composition of mineral oils in fiber and pulp. The composition of the mineral oils can be changed by, for example, breaking down or modifying the chemical structure of the mineral oils. The level of mineral oils can be decreased both by the breakdown of the mineral oils and by mobilizing and liberating the mineral oils so that the mineral oils and inks from the waste papers can be detached and separated from the fibers during pulp processing and papermaking. The resulting pulp and paper is suitable for making food packaging with much less or no mineral oil contamination.

It has been discovered that by treating pulp with the disclosed enzyme compositions, mineral oils on and in pulp fiber can be broken down, modified, liberated, and/or mobilized, which facilitates the removal of the mineral oils from the pulp. The modification and mobilization of mineral oils through treatment with the enzyme composition may be attributed to the unique biological activity of the enzyme composition, which can be effective to break down or modify the chemical structure of the mineral oils, break the fiber-ink component bonding, expand and swell pulp fibers, and dislodge the mineral oils on the fiber surface as well as within the fiber bundles, between the fibrils, or in the fiber lumens. The breakdown and modification of mineral oils can both increase their volatility and mobility in the fiber and pulp and convert problematic forms of the mineral oils. For example, enzyme compositions can chemically alter the mineral oils to more benign forms, such as by ring opening, lowering of the aromaticity, reducing saturation, and other chemical modifications to convert the mineral oils into less problematic forms.

A partial enzymatic hydrolysis of cellulose within the micro structure of the fiber surface may occur during the enzymatic reaction and the mineral oil can be mobilized and more easily liberated and removed during pulp processing or paper making process, such as during drying.

Disclosed are enzyme compositions comprising one or more enzymes from the alkane hydroxylase enzyme group, wherein the enzyme composition is formulated to treat the mineral oil and vegetable oil components in wastepaper stream, recycled pulp, virgin fiber, and paper products. Also disclosed are enzyme composition comprising one or more enzymes from the aromatic peroxygenase enzyme group, wherein the enzyme composition is formulated to treat the mineral oil and vegetable oil components in wastepaper stream, recycled pulp, virgin fiber, and paper products. Also disclosed are enzyme composition comprising one or more enzymes from the alkane hydroxylase enzyme group and one or more enzymes from the aromatic peroxygenase enzyme group, wherein the enzyme composition is formulated to treat the mineral oil and vegetable oil components in wastepaper stream, recycled pulp, virgin fiber, and paper products.

The enzyme composition can further comprise one or more enzymes from the fatty acid/alcohol oxidase enzyme group, the hydrolase enzyme group, the lyase enzyme group, or a combination. The enzymes from the alkane hydroxylase enzyme group are alkane hydroxylases. The enzymes from the alkane hydroxylase enzyme group can be, for example, alkane hydroxylase, alkane 1-hydroxylase, alkane 1-monooxygenase, cytochrome P450 alkane hydroxylase, and/or cytochrome P450 reductase. The enzyme from the aromatic peroxygenase enzyme group are aromatic peroxygenases. The enzyme from the aromatic peroxygenase enzyme group can be, for example, aromatic peroxygenase, mushroom peroxygenase, ring-hydroxylating dioxygenase, xylene monooxygenase, phenol 2-monooxygenase, laccase and/or catechol dioxygenase.

The enzyme from the aromatic peroxygenase enzyme group are aromatic peroxygenases. The enzymes from the fatty acid/alcohol oxidase enzyme group can be, for example, alcohol dehydrogenase, lauric acid omega-hydroxylase, fatty acid peroxygenase, long-chain alcohol oxidase and/or soybean peroxygenase. The enzymes from the hydrolase enzyme group are hydrolases. The enzymes from the hydrolase enzyme group can be, for example, phospholipase, lipase, esterase, amylase, cellulase, endo-glucanase, hemicellulase, xylanase, mannanase, gamanase, and/or pectinase. The enzymes from the lyase enzyme group are lyases. The enzymes from the lyase enzyme group can be, for example, pectin lyase and/or pectate lyase. The phospholipase(s) can be, for example, phospholipase A1, phospholipase A2, phospholipase B, phospholipase C, and/or phospholipase D.

Also disclosed are methods comprising applying the enzyme composition in a pulp or paper processing plant to produce pulp with modified, reduced, or eliminated mineral oil components. Also disclosed are methods comprising applying the enzyme composition in a pulp or paper processing plant to produce paper or paperboard products with modified, reduced, or eliminated mineral oil components. The application of the enzyme composition can be referred to as enzyme treatment. Also disclosed are methods of producing pulp with reduced mineral oil content and/or altered mineral oil composition by enzyme treatment is described. The method involves adding an enzyme composition capable of contacting and mobilizing mineral oils in the pulp. The mineral oils can be enzymatically modified in the pulp by the enzyme reaction with the ink vehicle. The detached and mobilized mineral oils can then be removed more easily from the resulting pulp containing medium in the mill processes due to better drainage at dewatering and papermaking processes. The altered mineral oil composition can result from chemical breakdown and modification of the mineral oils. Such breakdown and modification can convert the mineral oil components into less problematic forms.

The enzyme composition can be capable of breaking down, modifying, liberating, mobilizing, or a combination thereof, mineral oil components in the pulp. The enzyme composition can be capable of breaking down, modifying, liberating, mobilizing, or a combination thereof, vegetable oil components in the pulp. The enzyme composition can be capable of breaking down, modifying, liberating, mobilizing, or a combination thereof, mineral oil and vegetable oil components in the pulp.

The pulp or paper processing plant can be a virgin pulp plant, a wastepaper recycling plant, a papermaking plant, a tissue or towel producing plant, or a paperboard producing plant. The enzyme composition can be applied at one or more locations in the pulp or paper processing plant. For example, the enzyme composition is applied at one or more of the pulper, dump chest, stock chest, machine chest, fan pump, the head box, silo, saveall, and water system of the pulp or paper processing plant. As another example, the enzyme composition can be applied in one or more of the white water, clear white water, machine pit, or water treatment area of the pulp or paper processing plant. As another example, the enzyme composition can be applied in the dissolved air flotation (DAF) system of the pulp or paper processing plant. The enzyme composition applied in the DAF system of the pulp or paper processing plant can, for example, lower the mineral oil component levels in the water system to increase removal of mineral oil components from fibers in the final paper product.

Surfactant can be applied together with the enzyme composition. The surfactant be a single surfactant or can comprise a group of surfactants. The surfactant can, for example, increase removal of mineral oil components compared to the method when the surfactant is not applied.

One or more papermaking chemicals can be applied together with the enzyme composition. The papermaking chemicals can be one or more charge-inducing polymers suitable for use at a paper machine or dissolved air flotation (DAF) system to enhance the removal of mineral oil component in the method.

In some embodiments, the enzyme treatment in the methods can occur or be performed at an acidic and neutral pH conditions. For example, the treatment can occur or be performed at a pH between about 4.0 to less than 10. The enzyme composition can applied at a pH from 4.0 to 10.0. For example, the enzyme composition can applied at a pH from 4.0 to 8.0. The pH can also be controlled. For example, the pH can be controlled at a pH from about 4.5 to about 8.

The enzymes in the enzyme composition can be applied in the range of about 0.1 to 1000 IU per gram of oven dry (OD) fiber or pulp. For example, the enzymes in the enzyme composition can be applied in the range of about 1 to 250 IU per gram of oven dry (OD) fiber or pulp. As another example, the enzymes in the enzyme composition can be applied in the range of about 1 to 50 IU per gram of oven dry (OD) fiber or pulp.

The enzymes in the enzyme composition can be applied in the range of about 0.1 to 1000 IU per liter of process water. For example, the enzymes in the enzyme composition can be applied in the range of about 1 to 250 IU per liter of process water. As another example, the enzymes in the enzyme composition can be applied in the range of about 1 to 50 IU per liter of process water.

In some embodiments, the enzyme treatment can occur or be performed at a low or high consistency or both low and high consistency of pulp. In some embodiments, the enzyme treatment can occur or be performed for a period of less than about 1 hour or as long as over 24 hours. The enzyme composition can contact pulp or wastepaper after being applied for a time from 5 minutes to 24 hours. For example, the enzyme composition can contact pulp or wastepaper after being applied for a time from 5 minutes to 4 hours. As another example, the enzyme composition can contact pulp or wastepaper after being applied for a time from 10 to 25 minutes.

The enzyme composition can contact pulp or wastepaper at a temperature of from about 5° C. to about 85° C. For example, the enzyme composition can contact pulp or wastepaper at a temperature of from about 10° C. to 65° C. As another example, the enzyme composition can contact pulp or wastepaper at a temperature of from about 15° C. to 50° C. In some embodiments, the temperature of the enzyme treatment is in a range of from about 20° C. up to about 85° C. In some embodiments, the enzyme treatment can occur or be performed at a temperature in the range of from about 20° C. up to about 60° C. for a period of less than about 1 hour followed by a temperature in the range of from about 50° C. up to about 100° C. for a period of less than about 20 minutes.

The pulp or paper processing plant can process wastepaper, where the wastepaper is, for example, corrugated container paperboard. The pulp or paper processing plant can process old corrugated container (OCC), where the OCC furnish can comprise, for example, old newspaper (ONP), old magazine (OMG), and/or printing flyers printed with mineral oil and vegetable oil based inks. The pulp or paper processing plant can process pulp, where the pulp can comprise, for example, virgin pulp, recycled old corrugated container (OCC) pulp, recycled old newspaper (ONP) and old magazine (OMG), or a combination. The pulp or paper processing plant can process pulp, where the pulp can comprise, for example, recycled brown tissue and/or towel pulping source fiber.

The pulp or paper processing plant can produce paper, where the paper can be used for food packaging, food storage, food preparation, food serving, pizza boxes, plates, cups, eating utensils, napkins, paper towels, brown tissue or towel, tissue paper, toilet paper, and/or product packaging.

Also disclosed are methods of producing paper with reduced mineral oil content comprising:

(a) contacting pulp with an enzyme composition capable of breaking down, modifying, liberating, mobilizing, or a combination, mineral oil components in the pulp, and wherein the mineral oil components are modified by action of the enzyme composition; and (b) heating paper or wet web being formed from the pulp at a temperature and for a time sufficient to evaporate or sublimate some of the modified mineral oils from the forming paper.

The heating can be for a time sufficient to evaporate or sublimate some of the mobilized mineral oils is accomplished by using a sufficient number of drying cylinders.

Also disclosed are methods for producing pulp and paper products at a pulp or paper processing plant with reduced mineral oil content from waste paper, the method comprising the following sequential steps:

(a) pulping the wastepaper with mineral oil content above 25 ppm based on OD fiber with mill process water and an enzyme composition; wherein the enzyme composition comprises at least one or more enzymes from the hydrolase enzyme group (b) cleaning the pulp slurry through conventional cleaners;

(c) dewatering the pulp through a thickening stage and producing a final pulp, wherein the pulp has a Canadian Standard Freeness (CSF) of at least 25 ml greater than a pulp made by the same method but without the enzyme composition.

Also disclosed are methods for producing pulp and paper products at a pulp or paper processing plant with reduced mineral oil content from waste paper, the method comprising the following sequential steps:

(a) pulping the wastepaper with mineral oil content above 25 ppm based on OD fiber with mill process water and an enzyme composition; wherein the enzyme composition comprising at least one or more enzymes from the hydrolase enzyme group (b) cleaning the pulp slurry with conventional cleaners;

(c) washing the pulp slurry with a washer or thickener;

(d) making a paper product on a Fourdrinier paper machine with the dry line of the forming section moved at least 6 inches closer to the headbox when operating with the same settings as when not using the enzyme composition; and (e) drying the wet paper web through a conventional paper drying process.

Also disclosed is pulp produced by the disclosed method. Also disclosed is pulp produced using the disclosed enzyme composition. Also disclosed is paper produced from such pulp. Also disclosed is a paper product made from such pulp. The paper product can be, for example, food packaging, food storage, food preparation, food serving, pizza boxes, plates, cups, eating utensils, napkins, paper towels, brown tissue or towel, tissue paper, toilet paper, and/or product packaging.

In some embodiments, a desired amount of the enzymatically modified and mobilized mineral oils are removed from the pulp. The modified mineral oils can be removed from the pulp or paper by any suitable technique and unit operation in the mill process. For example, the modified mineral oils can be removed by flotation, by washing, or by a combination. They can also be removed through the significant dewatering step that occurs as paper is made. Mineral oils can also be removed through the drying process where they evaporate from fibers as the paper passes through the very hot drying section.

The enzyme composition can comprise enzymes that can help detach ink from pulp fibers, soften pulp fibers, swell pulp fibers, open pulp fibers, or their combinations, therefore making the minerals oils in the ink more easily removed. For example, the enzymes in the enzyme composition can include alkane hydroxylase and/or aromatic peroxygenase, optionally along with fatty acid/alcohol oxidase, hydrolase, and/or lyase, to chemically modify the mineral oil components and/or mobilize and/or liberate mineral oils from pulp fiber.

In some embodiments, the pulp can be derived from wood, fiber crops, non-wood sources, or a combination. In some embodiments, the non-wood source can comprise bamboo, reed, kenaf, wheat straw, rice straw, grass, or a combination. In some embodiments, the pulp can comprise waste printed paper or waste paper cartons that may or may not be printed or have labels affixed that have mineral oil based inks or adhesives.

The method can further comprise, prior to the enzyme treatment, pulping source fiber to form the pulp. In some embodiments, the source fiber can be derived from wood, fiber crops, non-wood sources, or a combination. In some embodiments, the source fiber can comprise virgin pulp, recycled pulp, or a combination. In some embodiments, the source fiber can comprise waste printed paper or waste paper cartons. In some embodiments, the source fiber can comprise wet lap pulp, dry lap pulp, or a combination.

The method can further comprise producing paper from the pulp. In some embodiments, the paper produced can be used for a product that comes into contact with a human. For example, the paper can be used for food packaging, food storage, food preparation, food serving, pizza boxes, plates, cups, eating utensils, napkins, paper towels, brown tissue or towel, tissue paper, toilet paper or other paper sanitary products, or product packaging. Thus, paper is described that is produced from pulp produced by the method. Paper products are described that are produced from pulp and paper produced by the method.

Also disclosed is pulp, paper, paper product produced by a disclosed method, where the mineral oil, MOAH, and/or MOSH content of the pulp, paper, or paper product is at least 25% less than pulp, paper, or paper product produced by the same method but without applying the enzyme composition.

Also disclosed is pulp produced by applying a disclosed enzyme composition in a pulp or paper processing plant to produce pulp, where the mineral oil, MOAH, and/or MOSH content of the pulp is at least 25% less than pulp, paper, or paper product produced by the same method but without applying the enzyme composition.

Also disclosed is paper or a paper product produced by applying a disclosed enzyme composition in a pulp or paper processing plant to produce paper or paperboard products, where the mineral oil, MOAH, and/or MOSH content of the paper or paper product is at least 25% less than paper or paper product produced by the same method but without applying the enzyme composition.

Also disclosed is pulp produced by applying an enzyme composition comprising one or more enzymes from the hydrolase enzyme group in a pulp or paper processing plant to produce pulp, where the mineral oil content of the pulp is at least 25% less than pulp produced by the same method but without applying the enzyme composition.

Also disclosed is paper or a paper product produced by applying an enzyme composition comprising one or more enzymes from the hydrolase enzyme group in a pulp or paper processing plant to produce paper or paperboard products, wherein the mineral oil content of the paper or paper product is at least 25% less than paper or paper product produced by the same method but without applying the enzyme composition.

In some embodiments, a method of producing paper with reduced mineral oil content is described. The method involves contacting pulp with an enzyme composition capable of modifying mineral oils in the pulp made from recycled paper. The mineral oils are modified in the pulp by contacting with the enzyme composition. The method can also involve contacting pulp with an enzyme composition capable of mobilizing mineral oils, including modified mineral oils, in the pulp made from recycled paper. The mineral oils are mobilized in the pulp by contacting with the enzyme composition.

Methods of producing recycled or virgin pulps and for using them in the manufacture of paper and paperboard products are also provided.

DETAILED DESCRIPTION OF THE INVENTION

The methods and compositions described herein provide a new way to reduce the mineral oil content of processed pulp and paper products and to convert the mineral oils into less problematic forms. The disclosed enzymatic conversion reduces adhesion of the mineral oils to paper fibers, increases the solubility of the mineral oils (thus aiding their separation from paper fibers, and converts the mineral oils into less problematic forms. Each of these improves the process of and product produced from paper recycling and pulp processing.

The disclosed methods and compositions can use various types of enzymes to break down and/or modify the mineral oil components in the wastepaper recycling and papermaking processes through enzymatic reaction such as alkane oxidation, aromatic ring bursting, degradation or modification of any mineral and vegetable oil components, which lead to physiochemical property changes for improved removal of the mineral oil portion. Such degradation or modification can also convert medically problematic minerals oils into less problematic compounds. For example, MOAH are considered more problematic than MOSH, MOH with rings are generally considered more problematic than MOH without rings, and more saturated MOH are considered more problematic than less saturated MOH. Thus, breakdown and modification of mineral oils to have less MOAH, lower aromaticity, less saturation, and/or fewer mineral oils with rings produces a less problematic mix of mineral oils.

The disclosed methods and compositions for reducing and converting mineral oils can be used as part of any suitable wastepaper processing and papermaking methods. Examples of such methods are described herein, and other processes for processing waste papers, virgin fibers or in making paper products from virgin or recycled fibers known to those of skill in the art can be used with the disclosed methods and compositions.

The disclosed compositions, components, and methods can include or result in a variety of features. Such features can be used to define the goal, capability, and/or operation of the enzyme compositions and/or methods. For example, there can be materially greater drainage on the paper machine forming section. As another example, enzymatic mechanisms of modifying or liberating mineral oils from the pulp stock can increase freeness in the paper machine headbox by at least 20 ml CSF (Canadian Standard Freeness) versus normal methods. As another example, use of the enzymatic treatment can move the dry line on the forming section table backwards toward the headbox by at least 6 inches due to improved drainage and water removal compared to the dry line position when not using the enzyme composition. As another example, there can be a greater freeness decrease (ml CSF drop) across the refining stage for a given kWh refining energy employed that is at least 5% greater than when not using the enzymatic treatment. As another example, the pulp stock can have higher pressed solids after the press section of at least 2% higher consistency before the drying section than without the enzymatic treatment. As another example, the paper machine whitewater consistency can have at least 5% less total suspended solids than without the enzymatic treatment. As another example, the fan pump speed can be at least 5% faster than without the enzymatic treatment for processing a similar ton per hour rate. As another example, the dissolved air flotation (DAF) clarifier accepts can be at least 5% lower in total suspended solids without the enzymatic treatment. As another example, there can be greater defiberization of wastepaper in the pulper as measured by a 5% greater reduction in gross contaminant rejections than without the enzymatic treatment. As another example, there can be a greater pulp stock thickening in the stock preparation stages due to increased drainage as measured by a 5% more thickening capacity than without the enzymatic treatment. Each of these features, and other features, can be combined in any combination. Each of these features can be used with enzyme compositions that include one or more enzymes from the fatty acid/alcohol oxidase enzyme group, the hydrolase enzyme group, the lyase enzyme group, or a combination, but not necessarily any enzyme from the alkane hydroxylase enzyme group or the aromatic peroxygenase enzyme group.

A. Definitions

Unless defined otherwise, all technical and scientific terms used herein have the same meanings as commonly understood by one of skill in the art to which the disclosed invention belongs. Publications cited herein and the materials for which they are cited are specifically incorporated by reference.

The term "deinking plant" or "wastepaper recycling plant" refers to a plant or mill that processes wastepaper into a recycled pulp which can be used to manufacture paper either onsite or offsite. Deinking plant removes various contaminants such as inks, fillers, coatings, and stickies/adhesives from wastepaper and produces clean recycled pulp to be used either onsite or offsite at paper machines.

The term "papermaking machine," "papermaking mill," "paper machine," or "paper mill" refers to a plant, mill, or machine that converts virgin or recycled pulp or fibers into a paper and paperboard product.

The term "paper processing plant" refers to a plant, mill, or machine that processes pulp, fibers, paper, or wastepaper. Deinking plants, pulping plants, and papermaking mills are examples of paper processing plants.

The term "pulp processing plant" refers to a plant, mill, or machine that processes pulp, fibers, paper, or wastepaper. Deinking plants and pulping plants are examples of pulp processing plants.

The term "paper" or "paper product" refers to any formed, dried product whether compressed, corrugated, laminated, coated, filled, etc. product made primarily from plant fiber.

The term "effective amount" refers to any amount which results in a predetermined or desired outcome. For example, an effective amount of an enzyme formulation intended to mobilize mineral oils means the amount of enzyme formulation which is effective to decrease residual mineral oil levels in pulp or the final sheet compared to pulps not treated with the same enzyme formulation under the same conditions.

The term "colloidal ink particles" refers to colloidal particles, in the pulping and papermaking system, including hydrophilic materials such as sizing, coating, clay, fines or even slimes, and hydrophobic substances such as either mineral oil, vegetable oil or their combination. These colloidal ink particles are generally stable in the water system, but they will be destabilized quickly due to any physiochemical changes of the water system including but not limited to process pH, temp, charge shock and enzymatic reactions.

The term "enzymatic fiber modification" refers to any alteration or modification of the pulp fibers or fines or the aqueous phase of the pulp stock slurry as a result of interaction with an enzyme. The modification can either be a direct or indirect result of the enzyme treatments.

The term of "CSF" or "pulp drainage" refers to Canadian Standard Freeness measured following TAPPI Test Method T 227, Technical Association of the Pulp and Paper Industry, 15 Technology Pkwy, Peachtree Corners, Ga. 30092.

The term "dry line" refers to the location on a forming section (for example, Fourdrinier paper machine) where the appearance of the wet web of paper changes abruptly as noted by reflection of light off the stock/water surface. Before the dry line, the stock web has a glossy, wet appearance. After the dry line the wet web appears dull. Increased freeness of the pulp tends to move the dry line in the direction of the headbox.

"Recycled pulp" or "recycled fibers" refers to the pulp or fiber stock components of a paper or paperboard furnish that is derived from recovered paper and paperboard or wastepaper.

"White mineral oils" are mineral oils that that exclusively consist of saturated components and are of such high molecular mass that uptake by humans is negligible (average relative mass at least 480 Da; less than 5% below n-$C_{25}$).

The term "normal method" when used in the context of pulp processing and papermaking refers to typical or industry standard methods when not using enzyme compositions. A useful form of normal method is a pulp processing or papermaking process that is the same as a disclosed method but without the use of a disclosed enzyme composition.

B. Compositions

Methods and compositions for mobilizing mineral oils and reducing the mineral oil content in pulp and paper products made from the pulp are described herein. The pulp fibers are treated with an enzyme composition to enzymatically break down and/or modify the mineral oil components or modify mineral oils present in and on the pulp fibers. The enzyme composition (and/or one or more separate enzyme compositions) can also be used to alter the pulp fibers to condition the properties of the pulp fibers and/or to deink the pulp fibers.

1. Enzyme Composition

Enzyme compositions for treatment of pulp in the wastepaper recycling mill, pulping and papermaking plants include one or more enzymes effective to breakdown, modify, liberate, and/or mobilize mineral oil components in pulp. Examples of enzymes that can be used to treat pulp as described herein include, but are not limited to, enzymes of alkane hydroxylase, aromatic peroxygenase, fatty acid/alcohol oxidase, hydrolase, lyase, expansin, and swollenin.

The enzyme compositions can be any mixture, blend, or combination of enzymes suitable for any of the purposes described herein. Generally, the enzymes in the enzyme compositions are not coupled or conjugated but rather are mixtures or blends of enzymes (and other components of the enzyme composition).

The enzyme compositions that react and modify mineral oil components include alkane hydroxylase, aromatic peroxygenase, fatty acid/alcohol oxidase, hydrolase and lyase. Alkane hydroxylase and aromatic peroxygenase target MOAH and MOSH of the mineral oils through modifications such that degradation, aromatic ring bursting or turning alkane into alcohols, while fatty acid/alcohol oxidase, hydrolase and lyase target fibers and DCS in water phase and their combinations, would enhance the removal of mineral oil from the pulping and paper making process.

The alkane hydroxylase group comprises alkane hydroxylases, alkane 1-hydroxylase, alkane 1-monooxygenase (for example, EC 1.14.15.3), Cytochrome P450 alkane hydroxylase (for example, EC 1.14.15.1) and cytochrome P450 reductase.

The aromatic peroxygenase group includes enzymes that may change the ring structures of MOAH to less problematic forms of MOAH. Enzymes in this group include aromatic peroxygenase (for example, EC1.11.2.1), mushroom peroxygenase, ring-hydroxylating dioxygenase, xylene monooxygenase, phenol 2-monooxygenase, laccase and catechol dioxygenase.

The fatty acid/alcohol oxidase enzymes include alcohol dehydrogenase, lauric acid omega-hydroxylase, fatty acid peroxygenase (for example, EC1.11.2.4), long-chain alcohol oxidase and soybean peroxygenase (for example, EC 1.11.2.3). The enzymes in this group can further convert the resultant acid and/or alcohol from the oxidization of MOSH into alcohol and acid forms, less hydrophobic non-toxic molecules, which would then be more easily removed. Also, the modifications of any vegetable oil portion in the mixture of mineral oil and vegetable oil, either on fiber surfaces, or in the fiber or in water phase, could enhance the removal of mineral oil components from virgin and recycled pulping processes.

The hydrolase group is a group of enzymes that target enzymatically modified mineral oil, fibers, fines and DCS in waste phase of pulp process. The enzyme group includes esterase, lipase, phospholipase, cellulase, hemicellulase, xylanase, amylase, pectinase and pectin lyase and pectate lyase. The phospholipase can be phospholipase A1, phospholipase A2, phospholipase B, phospholipase C, and/or phospholipase D.

The phospholipase enzymes in this group hydrolyze phospholipid components in the vegetable oil for improved detachment and modification of mineral oil and vegetable oil components and particles, which help the removal of MOAH and MOSH in the recycled paper board products for food grade packaging product. Phospholipase is one type of special lipases for phospholipids and this enzyme group has been used for food oil processing to lower the natural oil viscosity in the degumming process of oil production.

Hemicellulase is a category of enzymes that include enzymes capable of hydrolyzing hemicellulose polymers to shorter oligomers. Examples of hemicellulase include, but are not limited to, xylanase, gamanase, arabinase, and mannanase.

The enzyme composition can have various make ups as described herein. For example, the enzyme composition can comprise one or more enzymes from the alkane hydroxylase enzyme group. As another example, the enzyme composition can comprise one or more enzymes from the aromatic peroxygenase enzyme group. As another example, the enzyme composition can comprise one or more enzymes from the alkane hydroxylase enzyme group and one or more enzymes from the aromatic peroxygenase enzyme group. As another example, the enzyme composition can comprise one or more enzymes from the fatty acid/alcohol oxidase enzyme group, the hydrolase enzyme group, the lyase enzyme group, or a combination. As another example, the enzyme composition can comprise one or more enzymes from the alkane hydroxylase enzyme group and one or more enzymes from the fatty acid/alcohol oxidase enzyme group, the hydrolase enzyme group, the lyase enzyme group, or a combination. As another example, the enzyme composition can comprise one or more enzymes from the aromatic peroxygenase enzyme group and one or more enzymes from the fatty acid/alcohol oxidase enzyme group, the hydrolase enzyme group, the lyase enzyme group, or a combination. As another example, the enzyme composition can comprise one or more enzymes from the alkane hydroxylase enzyme group, one or more enzymes from the aromatic peroxygenase enzyme group, and one or more enzymes from the fatty acid/alcohol oxidase enzyme group, the hydrolase enzyme group, the lyase enzyme group, or a combination.

The enzymes are typically used in combination, although this is not essential and pulp may be treated with, for example, only one type of enzymes or one class of enzymes such as cellulases. In one embodiment, the enzyme composition is added in a concentration ranging from between 5 to 600 enzyme activity units per 100 g OD fibers. Preferably, the concentration of the enzymes is between 20 to 200 enzyme units/100 g OD of fibers. The enzyme units can be determined as described in US 20130146239 A1 patent application by James Tausche, et al. and expansin/swollenin content can be measured using the Micro Lowry Total Protein Kit with Peterson's modification using Sigma product TP0300 and L 3540 (St. Louis, Mo., USA). Swollenins and their sources are described in U.S. Pat. No. 6,967,246 to Swanson et al., which is incorporated herein by reference.

The enzyme compositions can be provided in the form of a solution or granulated enzymes that include compositions that adjust for pH and salt concentrations. In general, enzyme formulations can also include the appropriate buffer for optimal enzyme activity. One of skill in the art can optimize the conditions to maximize enzymatic activity using conventional techniques known in the art.

In some embodiments the enzymes may be introduced in a dried, granulated, encapsulated, or pelletized form. Stabilizers such as metal ions and harge-inducing polymers, such as cationic polymers, may optionally be added to the formulation. The enzyme formulations may be treated to improve storage stability. A method for producing solid granulates with improved storage stability is described for example U.S. Publication No. 2007/0111920 by Bauer, et al.

The enzyme compositions can also additional enzymes or other components. For example, the enzyme compositions can include one or more dispersants, which can be surfactants and/or polymers which may be used, for example, to enhance stability or activity of the enzymes.

2. Pulp and Paper Products

The enzyme compositions and methods can produce pulp. Such pulp can have a reduced level of mineral oils and/or less problematic forms of mineral oils (as compared to pulp produced without use of the enzyme compositions or methods). Pulp made using the enzyme compositions and methods can be described by the amount, level, composition, etc., of mineral oils as compared to the amount, level, composition, etc., of mineral oils prior to treatment. Pulp made using the enzyme compositions and methods can also be described by the amount, level, composition, etc., of mineral oils as compared to the amount, level, composition, etc., of mineral oils in pulp produced not using the enzyme compositions or methods.

In some embodiments, the mineral oils can be reduced in the pulp or paper by a desired amount or to a desired level. For example, the mineral oils in the pulp or paper can be reduced by various amounts depending on the level of mineral oils in the starting material, the nature of the mineral oils present, and the efficacy and magnitude of the enzymatic treatment. For example, the mineral oils in the pulp or paper can be reduced by at least 10%, 25%, 50%, or 80%, depending of the situation. As another example, the mineral oils in the pulp or paper can be reduced by 50% or more, 60% or more, 70% or more, 80% or more, 85% or more, 90% or more, 95% or more, 96% or more, 97% or more, 98% or more, or 99% or more. Reduction in mineral oil content and levels can be assessed by comparison to any suitable reference content or level. For example, reduction in mineral oil content or levels can be assessed in comparison to the mineral oil content or levels in pulp before the incubating step of the method. Such a reference is useful because it accounts for differing mineral oil content and levels in different pulps from different fiber sources.

For example, pulp, paper, or paper product produced by the disclosed methods can result in pulp, paper, or paper product where the mineral oil, MOAH, and/or MOSH content of the pulp, paper, or paper product is at least at least 10%, 25%, 50%, or 80% less, depending on the level of mineral oils in the starting material, the nature of the mineral oils present, and the efficacy and magnitude of the enzymatic treatment, as compared to pulp, paper, or paper product produced by the same method but without applying the enzyme composition.

As another example, pulp produced by applying a disclosed enzyme composition in a pulp or paper processing plant to produce pulp can result in pulp where the mineral oil, MOAH, and/or MOSH content of the pulp is at least 25% less than pulp produced by the same method but without applying the enzyme composition.

As another example, paper or a paper product produced by applying a disclosed enzyme composition in a pulp or paper processing plant to produce paper or paperboard products can result in paper or paper product where the mineral oil, MOAH, and/or MOSH content of the paper or paper product is at least 25% less than paper or paper product produced by the same method but without applying the enzyme composition.

As another example, pulp produced by applying an enzyme composition comprising one or more enzymes from the hydrolase enzyme group in a pulp or paper processing plant to produce pulp can result in pulp where the mineral oil content of the pulp is at least 25% less than pulp produced by the same method but without applying the enzyme composition.

As another example, paper or a paper product produced by applying an enzyme composition comprising one or more enzymes from the hydrolase enzyme group in a pulp or paper processing plant to produce paper or paperboard products can result in paper or paper product wherein the mineral oil content of the paper or paper product is at least 25% less than paper or paper product produced by the same method but without applying the enzyme composition.

As another example, the mineral oils in the pulp or paper can be reduced to less than 300 mg/kg, 200 mg/kg, 100 mg/kg, 50 mg/kg, or 25 mg/kg of OD fiber. These reductions can be for total mineral oils (both MOSH and MOAH), just MOSH, or just MOAH. For example, the reduction can be by 80% of MOSH and 90% of MOAH. Further, these reductions can be for certain specific other classes, type, or individual mineral oils. For example, the reduction can be to less than 50 mg/kg for $<C_{20}$ MOSH and less than 100 mg/kg for $>C_{20}<C_{28}$ MOSH. Unless otherwise indicated, the level of mineral oils and reductions in mineral oils refer to mineral oils up to n-$C_{28}$.

Also disclosed is paper produced from pulp produced using the enzyme compositions and methods. Also disclosed are paper products made from such pulp. The paper product can be, for example, food packaging, food storage, food preparation, food serving, pizza boxes, plates, cups, eating utensils, napkins, paper towels, brown tissue or towel, tissue paper, toilet paper, and/or product packaging. Paper and paper products can be described by the amount, level, composition, etc., of mineral oils as compared to the amount, level, composition, etc., of mineral oils in paper and paper products produced for pulp not using the enzyme compositions or methods.

C. Methods and Materials for Contacting With, Breaking Down and Modifying Mineral Oil Components Methods for reducing residual mineral oil levels of pulp are described. The methods include treating waste papers, pulp, or process water with an enzyme composition containing enzyme in an amount effective to break down or modify the mineral oil components and reduce residual mineral oil component levels in the pulp, the process water and paper products. The methods also include treating pulp at a paper making plant with an enzyme formulation containing enzyme in an amount effective to modify the formation and drying of any paper products which lead to better evaporation or sublimatation of mineral oils in and on the paper being formed.

The level of mineral oils can be determined using any suitable method. Useful methods for determining the level of mineral oils are those methods described in EFPRO, "Determination of Mineral Oil Content in Recycled Papers," 2012; Biedermann and Grob, Eur. Food Res. Technol. 230: 785-796 (2010); and Lorenzini et al., Food Additives and Contaminants, Part A, 27:1765-1774 (2010).

The pulp may optionally be treated with additives such as stabilizers and dispersants. These additives may be added alone or together with the enzymes at the same addition locations or separately at different locations.

The enzyme composition is typically applied as a solution to the pulp stock but could also be added in dried or granulated enzyme form. Timing, concentration, temperature, pH and pulp consistency all play a role in pulp processing. The stage of the process in which the enzyme treatment is applied can vary.

1. Treatment of Pulp With Enzyme Compositions

Several operating parameters in the pulp mill and paper mill such as temperature or pH can be varied to alter the enzyme activity and increase evaporation and sublimation of mineral oils in order to mobilize mineral oils and reduce residual mineral oil levels in the paper products.

i. Timing/Location of Enzyme Application

The point of the process in the paper recycling mill, deink plant, or paper machine at which the enzyme is applied is dependent on a variety of factors such as (1) the reaction time of the enzyme with the pulp; (2) the amount of time between the enzyme treatment and the drying or wet lapping step; and (3) the water loops in the pulp mill, deink plant, or paper machine. The reaction time of the enzyme composition with the pulp stock can vary. The pulp stock is treated with enzyme composition for at least 5 minutes or longer. In some embodiments, the pulp is treated for at least 5 minutes, at least 10 minutes, or at least 15 minutes. As examples, the pulp can be treated for 5 minutes to 24 hours, 10 minutes to 12 hours, 10 minutes to 6 hours, 20 minutes to 6 hours, 20 minutes to 5 hours, 20 minutes to 4 hours, 20 minutes to 3 hours, 20 minutes to 2 hours, 30 minutes to 6 hours, 30 minutes to 5 hours, 30 minutes to 4 hours, 30 minutes to 3 hours, or 30 minutes to 3 hours. The pulp is enzymatically treated for a period of time and in an amount and under conditions resulting in modification of mineral oils in the pulp.

The enzyme treatment can be performed in chests and tanks in the pulping and papermaking mill before the final dewatering or drying step; preferably as early as possible in the processes such as during pulping. The enzyme treatment can be applied to virgin fibers, recycled fibers or mixtures thereof. Other equipment stages in which the methods can be performed include, but are not limited to, dump chests, bleach towers, feed tanks, high density towers, silo water, white water tanks and other parts of the mill where a minimum of 5 minutes of contact time occurs or where process waters from the pre-drying or pre-wet lapping dewatering step return to a suitable part of the process for enzyme effect. The contact time can be longer. Generally, the time for contact can be a sufficient time to result in some or sufficient breakdown or modification of MOAH and MOSH.

The enzyme treatment can be performed in chests or tanks in the paper machine before the wire section or the felts; preferably during pulping (or re-pulping). Other equipment stages in which the methods can be performed include, but are not limited to, dump chests, feed tanks, silo water, white water tanks and other parts of the paper machine where a minimum of 5 minutes of contact time occurs or where process waters from the pre-drying or pre-wet lapping dewatering step return to a suitable part of the process for enzyme effect. The contact time can be longer. Generally, the time for contact can be a sufficient time to result in some or sufficient breakdown or modification of MOAH and MOSH.

ii. Temperature

It is well known in the art that enzyme activity is temperature and pH dependent. The enzyme treatments described herein are typically effective at temperatures of from 15° C. to 80° C. The more preferred temperature range for enzyme treatments is from about 20° C. to 60° C. However, the temperature range can vary depending on the nature of the enzyme used and the optimal activity range for each enzyme.

iii. pH

The pH of the pulp stock can generally be from about 3 to about 9.5 for most enzymes, more preferably from about 4.5 to 8.0. The pH of the stock can be adjusted using pH modifiers such as alum or aluminates, certain acids, carbon dioxide, and various alkalis such as sodium hydroxide.

iv. Enzyme Concentration

The enzyme dosage depends on the specific enzyme and the other treatment conditions, in particular pulp consistency and temperature.

The enzymes may be used alone or in combination. The enzymes' concentration preferably ranges between 5 to 600 enzyme units/100 g oven dried ("OD") fiber. Preferably, the concentration of the enzymes is between 20 to 200 enzyme units/100 g OD of fibers. The enzyme units can be determined as described herein. The effective amount of enzyme is that which results in reduced residual mineral oil levels in the pulp relative to non-enzyme treated pulp. The method can result in decreased residual mineral oil levels in paper made from the pulp.

2. Reduction of Mineral Oils in Pulp and Paper Products

The methods can decrease the level and/or change the composition of mineral oils in fiber and pulp. The composition of the mineral oils can be changed by, for example, breaking down or modifying the chemical structure of the mineral oils. The level of mineral oils can be decreased both by the breakdown of the mineral oils and by mobilizing and liberating the mineral oils so that the mineral oils and inks from the waste papers can be detached and separated from the fibers during pulp processing and papermaking. The resulting pulp and paper is suitable for making food packaging with much less or no mineral oil contamination.

The methods can reduce the mineral oil level and composition in pulp and paper products. Any reduction in the level or form of mineral oils in pulp and paper products is useful. Particularly useful would be reduction of mineral oil levels in paper products used for food packaging and storage to goal or target levels. For example, the Joint FAO/WHO Expert Committee on Food Additives (JECFA) provides detailed classification of mineral oil products (Joint FAO/WHO Expert Committee on Food Additives (JECFA)). For oils of high molecular mass, defined by an average relative mass of >500 Da and a carbon number at the 5% distillation point >28, an acceptable daily intake (ADI) of 0-20 mg/kg body weight (bw) was defined (Joint FAO/WHO Expert Committee on Food Additives (JECFA) (2002) 59th report), WHO Technical Report Series 913, pp 11-20). For medium and low viscosity mineral oils, three classes were specified. Class I (480-500 Da; 5% distillation point >25) corresponded to that evaluated by the EU Scientific Committee for Food (SCF) as mentioned above and an ADI of 10 mg/kg bw was established. For classes II and III, with average masses of 400-480 and 300-400 Da, respectively, and 5% distillation points at n-C22 and n-C17, respectively, a 1,000 times lower (temporary) ADI (0.01 mg/kg body weight) was set.

D. Pulp and Pulp Fibers

Pulp and paper with reduced residual mineral oil levels is obtained by treatment with an effective amount of an enzyme(s) to break down, and/or modify, and/or liberate, and/or mobilize mineral oil components and reduce residual mineral oil component levels compared to untreated pulps and sheets made from untreated pulp.

The pulp and pulp fibers can be derived from any of a number of sources. The source of the fiber in a pulp or paper can be referred to as the fiber source. Pulp can be made from wood, fiber crops or other non-wood sources such as wheat straw or rice straw or grass. Wood pulp comes from softwood and hardwood trees. Softwood trees include spruce, pine, fir, larch and hemlock. Hardwoods include eucalyptus, aspen and birch.

The pulp can be virgin pulp or recycled pulp. Virgin pulp is pulp that has never been made into a final paper product. Pulps could have been processed through a variety of methods, including but not limited to mechanical pulping, CTMP, unbleached kraft (e.g., NSSC, Carbonate cooking), and bleached kraft pulping. Recycled pulp refers to pulp that was recycled from waste paper such as through a deinking or recycling process.

The consistency of the pulp stock to be enzymatically treated can be between about 0.1% and 35%, more preferably between 0.5% and 10%. Consistency is defined as the oven dry weight of the fiber divided by the total weight of the fiber and water stock.

Enzymatic fiber modification can result from increasing fibrillation of fibers resulting in more hydrogen bonds on the fiber and greater physical entanglement. Enzymatic fiber modification can also swell the outer layer of the fiber, reducing its density, and therefore making the fibers more "refining-able" resulting in more fibrils and delamination of outside fiber walls when processed through a mechanical refiner.

The pulp having reduced residual mineral oil levels is re-pulped at a paper mill before manufacturing paper. The re-pulping can be performed using any re-pulping methods known in the art.

The present invention will be further understood by reference to the following non-limiting examples.

EXAMPLES

Example 1: Mineral Oil Removal from Old Newsprint Stock Using Enzymes

A newspaper containing mineral oil ink was collected, pulped at 5.0% for 7 minutes in a pulper, then treated with and without enzymes for 45 minutes at pH 6.0 and temperature of 45° C., and followed by dilution of stock to 1.0% and 3.0 gram pads were made afterwards. The pads were then processed with an extraction using hexane and the extractives were analyzed using GC and mass spectrometry following the procedures as outlined in the determination of hydrocarbons from mineral oil (MOSH &MOAH) in packaging materials and dry foodstuffs by solid phase extraction and GC-FID by the Kantonales Labor Zurich (KLZH; Official Food Control Authority of the Canton of Zurich) and the National Reference Laboratory for Food Contact Materials at the Federal Institute for Risk Assessment (BfR).

Many major publishing houses are using newsprint ink-containing soybean oil for environmental reason instead of mineral oil which would not contribute to the mineral oil presence in the wastepaper stream, while many small newspapers are printed with mineral oil based inks for economic reasons and the mineral oil contaminated newspaper ends in wastepaper stream. Table 1 shows the general chemical composition of newsprint inks. Table 2 shows the removal of mineral oil from old newspaper (ONP) using enzymes through one stage of washing and sheet forming The cytochrome P450 reductase (EC 1.6.2.4), Sigma-Aldrich c4839, is of the alkane hydroxylase variety, while a few commercial esterases such as Stickaway®, NovoCor ADL and starch modification enzyme Finizym® W and laccase from Novozymes and phospholipase such as Lyso-Max® oil from DuPont are used individually or in combinations.

TABLE 1

General Chemical Composition of Newsprint Ink

| Components | Percentages |
| --- | --- |
| Pigment | 10-20% |
| Resins | 10-25% |

TABLE 1-continued

General Chemical Composition of Newsprint Ink

| Components | Percentages |
|---|---|
| Clay/Fillers | 5-15% |
| Rheological Additives | 1-5% |
| Lithographic Control Additives | 1-5% |
| Petroleum (Mineral) or Vegetable Oil | 30-65% |

TABLE 2

Enzymes on mineral oil removal from old newspaper

| | Treatments | Mineral oil content, ppm | Mineral oil reduction, % |
|---|---|---|---|
| Enzymes | Control | 2886 | n/a |
| | Esterase | 144 | 95.0 |
| | Phospholipase | 118 | 96.0 |
| | Cellulase | 769 | 73.4 |
| | Alkane hydroxylase | 243 | 92.0 |

Example 2: Mineral Oil Removal from Old Corrugated Container Board Stock of a Paperboard Recycling Mill Using Enzymes An OCC recycling paper mill using locally collected OCC including curbside collection with a large amount of old newspaper makes food grade products such as pizza box and cereal boxes. Due to the presence of mineral oil in old newspaper, old magazine and on OCC box printing and labels, there is a high amount of mineral oil presented in the mill system with mineral oil level at about 400 to 3,000 ppm at the machine chest based on OD fiber. A machine chest stock was collected after the pulper with enzymatic treatments following the same procedure as in Example 1 and the results are shown in Table 3.

Modification of mineral oil and vegetable oil by enzymes such as alkane hydroxylase, cellulase and phospholipase are also listed in Table 3. Also, the combinations of enzymes were used to treat the same stock and the mineral oil content in the treated stock was reduced further as in Table 3.

TABLE 3

Enzyme compositions on mineral oil removal from old corrugated container board

| | Treatments | Mineral oil content, ppm | Mineral oil reduction, % |
|---|---|---|---|
| | Control | 243 | |
| Enzymes and enzyme blends | Esterase | 70 | 71.1 |
| | Phospholipase | 62 | 74.4 |
| | Alkane hydroxylase | 85 | 65.0 |
| | Cellulase | 104 | 57.1 |
| | Alkane hydroxylase + esterase | 50 | 79.4 |
| | Alkane hydroxylase + Phospholipase | 35 | 85.6 |
| | Alkane hydroxylase + Cellulase | 31 | 87.2 |

Those skilled in the art will recognize, or be able to ascertain impact from, using no more than routine experimentation and equivalents to the specific embodiments of the invention described herein. Such equivalents are intended to be encompassed by the following claims.

We claim:

1. A method comprising
   applying an enzyme composition to a pulp in a pulp or paper processing plant,
   wherein the enzyme composition comprises one or more enzymes from the alkane hydroxylase enzyme group free of peroxygenase enzymes, and
   wherein the pulp is used to produce pulp, paper, or paperboard products with modified, reduced, or eliminated mineral oil components.

2. The method of claim 1, wherein the enzyme composition is formulated to treat the mineral oil and vegetable oil components in the wastepaper stream, recycled pulp, virgin fiber, and paper products.

3. The method of claim 1, wherein the enzyme composition further comprises one or more enzymes from the aromatic peroxygenase enzyme group, the fatty acid/alcohol oxidase enzyme group, the hydrolase enzyme group, the lyase enzyme group, or a combination thereof.

4. The method of claim 3, wherein the one or more enzymes from the aromatic peroxygenase enzyme group are selected from the group consisting of aromatic peroxygenase, mushroom peroxygenase, ring-hydroxylating dioxygenase, xylene monooxygenase, phenol 2-monooxygenase, laccase and catechol dioxygenase.

5. The method of claim 3, wherein the one or more enzymes from the fatty acid/alcohol oxidase enzyme group are selected from the group consisting of alcohol dehydrogenase, lauric acid omega-hydroxylase, fatty acid peroxygenase, long-chain alcohol oxidase and soybean peroxygenase.

6. The method of claim 3, wherein the one or more enzymes from the hydrolase enzyme group are selected from the group consisting of phospholipase, lipase, esterase, amylase, cellulase, endo-glucanase, hemicellulase, xylanase, mannanase, gamanase, and pectinase.

7. The method of claim 3, wherein the one or more enzymes from the lyase enzyme group are selected from the group consisting of pectin lyase and pectate lyase.

8. The method of claim 6, wherein the phospholipase is elected from the group consisting of phospholipase A1, phospholipase A2, phospholipase B, phospholipase C, and phospholipase D.

9. The method of claim 1, wherein the one or more enzymes from the alkane hydroxylase enzyme group are selected from the group consisting of alkane hydroxylase, alkane 1-hydroxylase, alkane 1-monooxygenase, cytochrome P450 alkane hydroxylase, and cytochrome P450 reductase.

10. The method of claim 1, wherein the pulp or paper processing plant is a virgin pulp plant, a wastepaper recycling plant, a papermaking plant, a tissue or towel producing plant, or a paperboard producing plant.

11. The method of claim 1, wherein the enzyme composition is applied at one or more of the pulper, dump chest, stock chest, machine chest, fan pump, the head box, silo, save-all, and water system of the pulp or paper processing plant.

12. The method of claim 1, wherein the enzyme composition is applied to the water system of the pulp or paper processing plant, wherein the enzyme composition is applied in one or more of the white water, clear white water, machine pit, the dissolved air flotation (DAF) system, or water treatment area of the pulp or paper processing plant.

13. The method of claim 12, wherein the enzyme composition enables increased removal of mineral oil components from fibers in the final paper product.

14. The method of claim 1, wherein surfactant is applied together with the enzyme composition, wherein the surfactant comprises a single surfactant or a group of surfactants, wherein the surfactant increases removal of mineral oil components compared to the method when the surfactant is not applied.

15. The method of claim 1, wherein one or more papermaking chemicals are applied in the pulp or paper processing plant, wherein the papermaking chemicals are one or more charge-inducing polymers suitable for use at a paper machine or dissolved air flotation (DAF) system to enhance the removal of mineral oil component in the method.

16. The method of claim 1, wherein the enzyme composition contacts pulp or wastepaper at a temperature of from about 5° C. to about 85° C.

17. The method of claim 1, wherein the pulp comprises wastepaper, wherein the wastepaper comprises one or more of old corrugated container (OCC), old newspaper (ONP), old magazine (OMG), and other wastepapers printed with or containing mineral oil and vegetable oil based inks.

18. The method of claim 1, wherein the pulp or paper processing plant processes pulp, wherein the pulp comprises virgin pulp, recycled pulp, or a combination thereof.

19. The method of claim 1, wherein the pulp or paper processing plant produces paper, wherein the paper is used for food packaging, food storage, food preparation, food serving, pizza boxes, plates, cups, eating utensils, napkins, paper towels, brown tissue or towel, tissue paper, toilet paper, or product packaging.

20. The method of claim 1, wherein the enzyme composition is capable of breaking down, modifying, liberating, mobilizing, or a combination thereof, residual mineral oil components in the pulp.

21. The method of claim 1, wherein the pulp comprises mineral oil components from wastepapers printed with mineral oil or vegetable oil based inks or from pulp, paper, or paperboard manufacturing sources.

22. The method of claim 1, wherein mineral oil content of the pulp, paper, or paperboard products is reduced by at least 10% relative to the pulp, paper, or paperboard products produced by the same method but without applying the enzyme composition.

23. A method of producing paper with reduced mineral oil content comprising:
 (a) contacting pulp with an enzyme composition comprising at least one or more enzymes from the alkane hydroxylase enzyme group free of peroxygenase enzymes and one or more enzymes from the aromatic peroxygenase enzyme group, the fatty acid/alcohol oxidase enzyme group, the hydrolase enzyme group, the lyase enzyme group, or a combination thereof, capable of breaking down, modifying, liberating, mobilizing, or a combination thereof, mineral oil components in and on fibers in the pulp, and wherein the mineral oil components are modified or liberated by action of the enzyme composition; and
 (b) forming paper from the pulp;
 wherein the formed paper has a mineral oil content at least 25% less than paper produced by the same method but without applying the enzyme composition.

24. The method of claim 23, wherein the enzyme composition is formulated to treat the mineral oil and vegetable oil components in the wastepaper stream, recycled pulp, virgin fiber, and paper products.

25. The method of claim 23, wherein the pulp or paper processing plant is a virgin pulp plant, a wastepaper recycling plant, a papermaking plant, a tissue or towel producing plant, or a paperboard producing plant.

26. The method of claim 23, wherein the enzyme composition is applied at one or more of the pulper, dump chest, stock chest, machine chest, fan pump, the head box, silo, save-all, and water system of the pulp or paper processing plant.

27. The method of claim 23, wherein the enzyme composition is applied to the water system of the pulp or paper processing plant, wherein the enzyme composition is applied in one or more of the white water, clear white water, machine pit, the dissolved air flotation (DAF) system, or water treatment area of the pulp or paper processing plant.

28. The method of claim 27, wherein the enzyme composition enables increased removal of mineral oil components from fibers in the final paper product.

29. The method of claim 23, wherein surfactant is applied together with the enzyme composition, wherein the surfactant comprises a single surfactant or a group of surfactants, wherein the surfactant increases removal of mineral oil components compared to the method when the surfactant is not applied.

30. The method of claim 23, wherein one or more papermaking chemicals are applied in the pulp or paper processing plant, wherein the papermaking chemicals are one or more charge-inducing polymers suitable for use at a paper machine or dissolved air flotation (DAF) system to enhance the removal of mineral oil component in the method.

31. The method of claim 23, wherein the enzyme composition contacts pulp or wastepaper at a temperature of from about 5° C. to about 85° C.

32. The method of claim 23, wherein the pulp comprises wastepaper, wherein the wastepaper comprises one or more of old corrugated container (OCC), old newspaper (ONP), old magazine (OMG), and other wastepapers printed with or containing mineral oil and vegetable oil based inks.

33. The method of claim 23, wherein the pulp or paper processing plant processes pulp, wherein the pulp comprises virgin pulp, recycled pulp, or a combination thereof.

34. The method of claim 23, wherein the pulp or paper processing plant produces paper, wherein the paper is used for food packaging, food storage, food preparation, food serving, pizza boxes, plates, cups, eating utensils, napkins, paper towels, brown tissue or towel, tissue paper, toilet paper, or product packaging.

35. The method of claim 23, wherein the enzyme composition is capable of breaking down, modifying, liberating, mobilizing, or a combination thereof, residual mineral oil components in the pulp.

36. The method of claim 23, wherein the formed paper has a mineral oil content at least 50% less than to paper produced by the same method but without applying the enzyme composition.

37. A method comprising
 applying an enzyme composition to a wastepaper or recycled pulp in a pulp or paper processing plant,
 wherein the enzyme composition comprises one or more enzymes from the alkane hydroxylase enzyme group free of peroxygenase enzymes, and
 wherein the wastepaper or the recycled pulp is used to produce pulp, paper, or paperboard products with modified, reduced, or eliminated mineral oil components.

38. The method of claim 37, wherein the one or more enzymes from the alkane hydroxylase enzyme group comprise enzymes selected from the group consisting of alkane hydroxylases, alkane 1-hydroxylase, alkane 1-monooxygenase, cytochrome P450 alkane hydroxylase, and cytochrome P450 reductase.

39. The method of claim 37, wherein the enzyme composition further comprises one or more enzymes from the aromatic peroxygenase enzyme group, the fatty acid/alcohol oxygenase enzyme group, the hydrolase enzyme group, the lyase enzyme group, or a combination thereof.

40. The method of claim 37, wherein the mineral oil content of the pulp, paper, or paperboard products is reduced by at least 10% relative to the pulp, paper, or paperboard products produced by the same method but without applying the enzyme composition.

41. A method for producing pulp and paper products at a pulp or paper processing plant with reduced mineral oil content from waste paper, the method comprising the following sequential steps:
(a) pulping the wastepaper with mineral oil content above 25 ppm based on OD fiber with mill process water and an enzyme composition;
wherein the enzyme composition comprises at least one or more enzymes from the hydrolase enzyme group and one or more enzymes from the alkane hydroxylase enzyme group free of peroxygenase enzymes;
(b) cleaning the pulp slurry through conventional cleaners;
(c) dewatering the pulp through a thickening stage and producing a final pulp wherein the pulp has a Canadian Standard Freeness (CSF) of at least 25 ml greater than a pulp made by the same method but without the enzyme composition; and
wherein the mineral oil content of the pulp is reduced by at least 50% relative to the pulp produced by the same method but without applying the enzyme composition.

42. The method of claim 41, wherein the enzyme composition further comprises one or more enzymes from the aromatic peroxygenase enzyme group, fatty acid/alcohol oxidase enzyme group, the lyase enzyme group, or a combination thereof.

43. A method for producing pulp and paper products at a pulp or paper processing plant with reduced mineral oil content from waste paper, the method comprising the following sequential steps:
(a) pulping the wastepaper with mineral oil content above 25 ppm based on OD fiber with mill process water and an enzyme composition;
wherein the enzyme composition comprises at least one or more enzymes from the hydrolase enzyme group and one or more enzymes from the alkane hydroxylase enzyme group free of peroxygenase enzymes;
(b) cleaning the pulp slurry with conventional cleaners;
(c) washing the pulp slurry with a washer or thickener;
(d) making a paper product on a Fourdrinier paper machine with the dry line of the forming section moved at least 6 inches closer to the headbox when operating with the same settings as when not using the enzyme composition; and
(e) drying the wet paper web through a conventional paper drying process;
wherein the mineral oil content of the formed paper is reduced by at least 50% relative to the paper produced by the same method but without applying the enzyme composition.

44. The method of claim 43, wherein the enzyme composition further comprises one or more enzymes from the aromatic peroxygenase enzyme group, fatty acid/alcohol oxidase enzyme group, the lyase enzyme group, or a combination thereof.

* * * * *